United States Patent [19]

Clovis et al.

[11] 4,040,913
[45] Aug. 9, 1977

[54] RECOVERY OF METHACRYLIC ACID FROM THE EFFLUENT OBTAINED FROM THE CONDENSATION OF FORMALDEHYDE AND PROPIONIC ACID

[75] Inventors: James S. Clovis, Morrisville; Jerome Dohling, Huntingdon Valley, both of Pa.; Francis J. Nicastro, Cherry Hill, N.J.

[73] Assignee: Rohm and Haas Company, Philadelphia, Pa.

[21] Appl. No.: 609,337

[22] Filed: Sept. 2, 1975

[51] Int. Cl.$^2$ .......................... B01D 3/34; C07C 57/04
[52] U.S. Cl. ........................................ 203/69; 203/70; 203/77; 203/91; 260/526 N
[58] Field of Search ............... 203/8, 15, 17, 39, 69, 203/77, 81, 91, 68; 210/21; 260/526 N

[56] References Cited

U.S. PATENT DOCUMENTS

| | | | |
|---|---|---|---|
| 2,475,959 | 7/1949 | Hasche | 203/17 |
| 3,247,248 | 4/1966 | Sims | 260/526 N |
| 3,414,485 | 12/1968 | Speed | 203/15 |
| 3,433,831 | 3/1969 | Yomiyama | 260/526 N |
| 3,781,332 | 12/1973 | Sato | 260/526 N |
| 3,798,264 | 3/1974 | Kubota | 203/15 |
| 3,844,903 | 10/1974 | Willersinn | 203/69 |

FOREIGN PATENT DOCUMENTS 1,167,793  10/1969  United Kingdom ............ 260/526 N Primary Examiner—Hiram H. Bernstein

[57] ABSTRACT

A process for the recovery of methacrylic acid from an aqueous effluent obtained by the vapor phase condensation of formaldehyde and propionic acid, where the effluent further contains unreacted formaldehyde and unreacted propionic acid, and where the recovery steps include: extracting the effluent with an organic solvent capable of azeotroping with propionic acid to obtain an organic phase and an aqueous raffinate; distilling the organic phase to remove 50-100% of the unreacted propionic acid and leaving as bottoms remaining unreacted propionic acid and methacrylic acid; distilling the methacrylic/propionic acid bottoms to obtain remaining unreacted propionic acid overhead and pure methacrylic acid as bottoms; distilling the aqueous raffinate with an entrainer to obtain dilute aqueous formaldehyde overhead and about 50% aqueous formaldehyde as bottoms; and distilling the dilute aqueous formaldehyde taken overhead to concentrate it to about 35% aqueous concentration.

13 Claims, 1 Drawing Figure

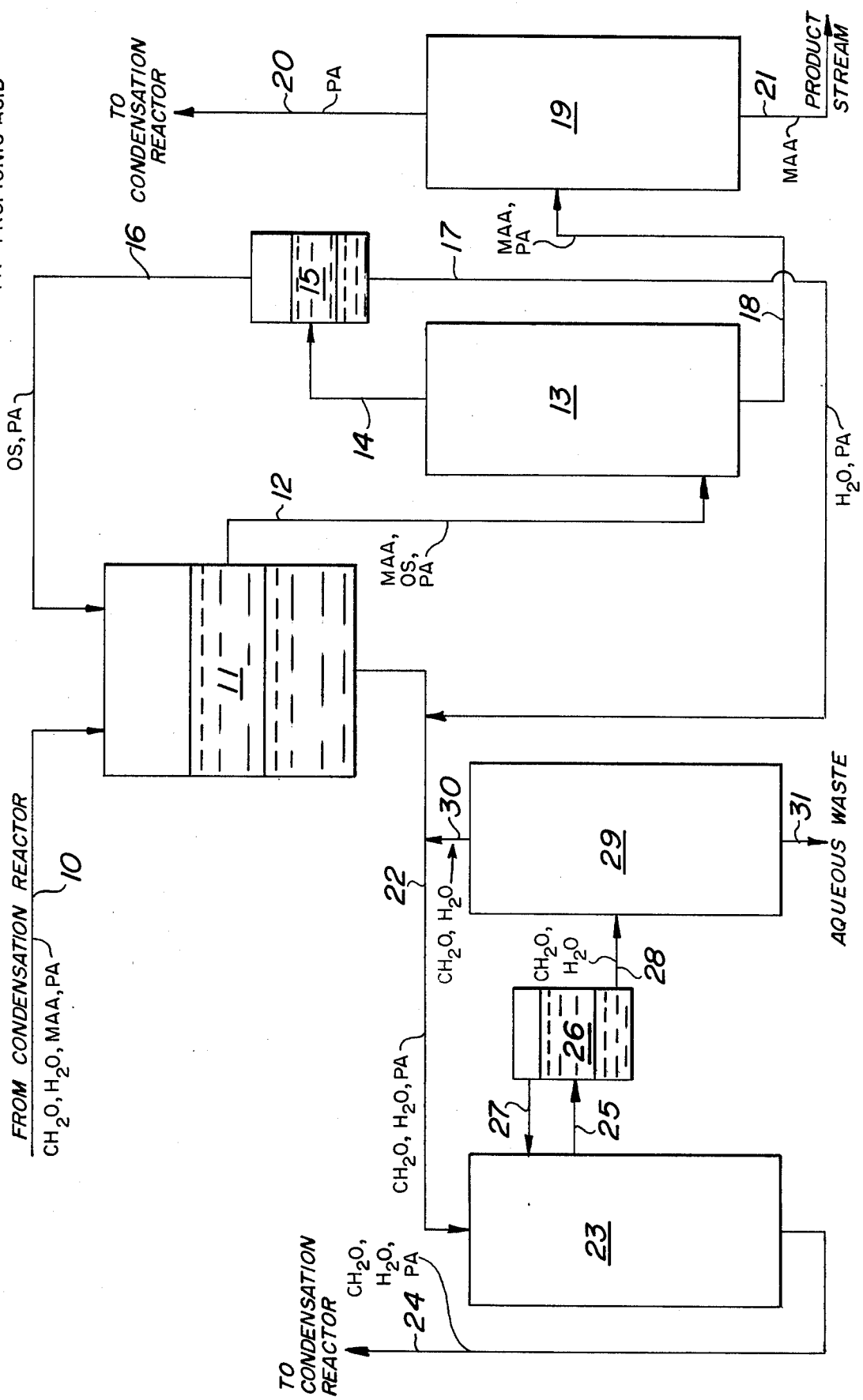

RECOVERY OF METHACRYLIC ACID FROM THE EFFLUENT OBTAINED FROM THE CONDENSATION OF FORMALDEHYDE AND PROPIONIC ACID

This invention relates to a process for recovery of methacrylic acid from an aqueous effluent obtained by vapor phase reaction of propionic acid and formaldehyde, as well as recovery and recycle of unreacted formaldehyde and propionic acid.

Methacrylic acid can be obtained from a number of different reaction paths, among which is condensation of propionic acid with formaldehyde in the vapor phase. The reaction is as follows:

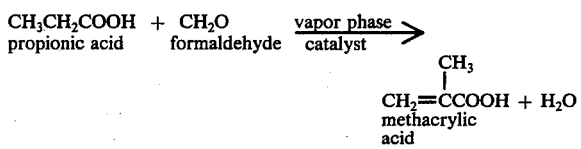

From this reaction, it can be seen that the desired product, methacrylic acid, is obtained in an aqueous stream which in addition to water and product, contains unreacted propionic acid, unreacted formaldehyde and various by-products. The basic requirement of the recovery process would be to separate the methacrylic acid in a state of relative purity (for example, of a propionic acid content of less than 0.1%) and at the same time to recover as much of the unreacted reactants for recycle and consequent reaction to produce further methacrylic acid. Another major function would be to separate excess water from the process thereby giving only one waste stream containing very little organic material.

However, separation of the complex mixture of this reaction is complicated by several factors. Firstly, all the components are highly soluble in water, making any simple separation scheme extremely unlikely. Secondly, the unreacted reactants must be recoverable in order to prevent costly and unnecessary waste of starting materials. Thirdly, propionic acid and methacrylic acid have boiling points that are very close-together, again making a simple fractional distillation separation scheme highly undesirable due to excessive loss of product. Fourthly, both formaldehyde and methacrylic acid have a marked tendency to polymerize, especially in environments such as are met with in distillations. Fifthly, very often when extraction processes are used, unextracted product is lost to the raffinate, which is often disposed of rather than being processed. And finally, very often in extraction processes a large aqueous waste stream results that is highly contaminated with organics, thereby giving rise to loss of organics as waste. Thus, it seems clear that conventional separations schemes are of little value for the contemplated recovery. However, the present invention effectively overcomes all these problems and does so with a minimal amount of steps.

The process for recovery of methacrylic acid from an aqueous effluent produced by the vapor phase condensation of formaldehyde and propionic acid, with the effluent further containing unreacted propionic acid and formaldehyde involves the steps of: (a) contacting the aqueous effluent with an organic solvent capable of azeotroping with propionic acid to obtain an organic layer and an aqueous raffinate; (b) distilling the organic layer obtained in step (a) to azeotropically remove about 50–100% of the unreacted propionic acid extracted by the organic solvent, and to strip off the organic solvent leaving as bottoms a mixture of methacrylic acid and remaining unreacted propionic acid; (c) distilling the bottoms of step (b) to obtain any remaining propionic acid overhead and pure methacrylic acid as bottoms; (d) azeotropically distilling the aqueous raffinate of step (a) with an entrainer to obtain water and formaldehyde overhead and formaldehyde/propionic acid bottoms; and (e) distilling the water/formaldehyde overhead obtained in step (d) to concentrate the formaldehyde for recycle to step (d), while disposing of the aqueous bottoms as waste.

The first step in the recovery process is contacting the aqueous effluent with an organic solvent capable of azeotroping with propionic acid so as to extract the methacrylic acid and unreacted propionic acid and thereby obtain an organic layer and an aqueous raffinate composed largely of formaldehyde and water. Any attempt to separate formaldehyde and water from propionic acid and methacrylic acid by distillation incurs the immediate problems of polymerization of formaldehyde to paraformaldehyde and that of taking methacrylic acid overhead with the formaldehyde and water, resulting in serious product loss. Thus, a solvent recovery is used as a first step.

A suitable solvent should: (1) have a high extractive efficiency for methacrylic acid and a low extractive efficiency for formaldehyde and water; (2) be easily separated from methacrylic acid by distillation; (3) give preferential extraction of methacrylic acid over propionic acid; and (4) form a low boiling azeotrope with propionic acid so that methacrylic acid can be freed of propionic acid concurrently with solvent stripping. Benzene, cyclohexane, mixtures of the two, xylene and n-octane have been found to meet all these requirements, with xylene and n-octane being preferred because they form azeotropes having very high propionic acid content, especially the xylene. The solvents can be used in varying solvent to solute weight ratios, such as 0.27 to 0.75, and the preferred ratio is 0.4. At the latter ratio, solvent stripping to recover solvent, such as xylene, also removes azeotropically about 70% of the unreacted propionic acid. The extraction is carried out by conventional means and at equilibrium a two layer system is obtained, one an organic layer, containing about 99% of the methacrylic acid and 85–95% of the unreacted propionic acid in xylene, while the second layer, the aqueous raffinate, contains a majority of the water of the effluent, the remaining unreacted propionic acid, traces of methacrylic acid and over 95% of the unreacted formaldehyde.

The organic layer is then subjected to extract stripping, which in addition to removing the organic solvent also azeotropically removes 50–100% of the unreacted propionic acid and traces of methacrylic acid, all traces of water and formaldehyde are also taken overhead. This distillation is preferably carried out at a reduced pressure of about 180–200 mm Hg and a preferred bottoms temperature of about 115°–125° C. The overhead distillate separates into two layers, the upper contains over 95% of the organic solvent, about 90–95% of the unreacted propionic acid taken overhead, traces of water, and some formaldehyde and methacrylic acid. This upper layer is recycled to the extraction step for further use as organic extraction solvent. The lower layer contains remaining unreacted propionic acid taken overhead, almost all the unreacted formaldehyde taken overhead, water and traces of methacrylic acid and organic solvent. This lower layer is processed with the aqeuous raffinate obtained in the extraction step.

The bottoms left after removal of organic solvent and azeotrope consist of the methacrylic acid and any propionic acid extracted but not taken overhead in the azeotrope. As a result of the removal of large quantities of unreacted propionic acid by azeotroping, there is an effective increase in the difference in boiling points of methylacrylic acid and propionic acid. This then allows a simple fractional distillation to be carried out whereby the overhead contains any remaining unreacted propionic acid extracted but not taken overhead and less than 5% of the methacrylic acid. This distillation is carried out at a reduced pressure of about 100 mm Hg and temperatures in the range of 112°-115° C. and yields a bottoms stream of esterification grade methacrylic acid containing only about 0.1% propionic acid. If the recovery process is carried out in a continuous manner, any remaining unreacted propionic acid taken overhead is recycled to the condensation reactor for further reaction to methacrylic acid.

The aqueous raffinate obtained during the extraction of the effluent from the reactor is processed so as to concentrate the formaldehyde contained therein without at the same time causing the formaldehyde to polymerize. The water, which must be removed, comes from two sources. Thus, for example, 50% aqueous formaldehyde has a water to formaldehyde molar ratio of 1.67:1. Every mole of formaldehyde that is reacted gives rise to a mole of water. Thus, each mole of 50% aqueous formaldehyde that reacts gives rise to 2.67 moles of water. If this water is not removed, it will be recycled, further diluting the formaldehyde and also reducing selectivity to methacrylic acid. In order to achieve the desired concentration, a two stage distillation is necessary, with the first stage employing an entrainer. The use of an entrainer has several important advantages in concentrating the unreacted formaldehyde. On the one hand, by lowering the distillation temperature, the formation of formaldehyde monohydrate (methylene glycol) is favored, allowing for more effective removal of water since the volatility of the formaldehyde is reduced. Also, the unreacted propionic acid not extracted into the organic layer during the extraction process and remaining in the raffinate must be taken into account in the concentration steps. By using an entrainer the water/entrainer azeotrope is removed overhead, while the propionic acid/water azeotrope remains behind as bottoms. The entrainer, then, removes water overhead as an azeotrope, while leaving behind concentrated formaldehyde and any unreacted propionic acid not originally extracted by the organic solvent in the effluent extraction step.

The azeotropic distillation of the raffinate is preferably carried out at a pressure in the range of about 100–400 mm Hg and temperatures in the range of 60°-90° C. The useful entrainers include benzene, toluene and methyl isobutyl ketone. The overhead azeotrope of this distillation is two phase. The organic phase with the entrainer is returned to the distillation column, while the aqueous phase, containing about 16% aqueous formaldehyde, is further concentrated in the second distillation. The bottoms are approximately 50% aqueous formaldehyde along with any unreacted propionic acid and methacrylic acid not originally extracted from the effluent. When the process is carried out continuously, the bottoms can be recycled to the condensation reactor to produce further methacrylic acid.

The aqueous phase of the overhead obtained in the azeotropic distillation of the raffinate is subjected to further distillation to concentrate the approximately 16% aqueous formaldehyde solution contained therein to about 35% aqueous formaldehyde. Here, concentrated formaldehyde is taken overhead and the bottoms disposed of as aqueous waste. It is important to note that by not taking any propionic acid overhead during the azeotropic distillation of the raffinate, some clearly desirable results are obtained. Firstly, the absence of propionic acid in the overhead distillate of the azeotropic distillation of the raffinate allows for easier recovery of the dilute formaldehyde contained therein. Thus, in the second distillation, concentrated formaldehyde can be taken overhead with no interfering co-distillation of propionic acid, and with no need for an entrainer. Secondly, if propionic acid is present, and formaldehyde is selectively taken overhead, the propionic acid will remain in the bottoms and thus will be lost as a part of the waste. This can be avoided by taking no propionic acid overhead during the azeotropic distillation of the raffinate.

This second and final formaldehyde concentration step is preferably run at a pressure of about 2600 mm Hg gauge and a reflux ratio of about 15:1. The distillate can either be recycled to the azeotropic column of the first formaldehyde concentration step for processing along with raffinate, or the formaldehyde contained therein can be used in other processes, such as for example, in the production of hexamethyllene tetramine. In any event, the concentration of formaldehyde in the overhead should be equal to or greater, on an aqueous basis, than that fed to the first concentration step.

A very important result of this two-stage formaldehyde concentration is that by taking very little formaldehyde overhead (and that only during the second concentration step) the formaldehyde is always handled in a relatively diluted stream, thereby minimizing the tendency of formaldehyde to polymerize.

It is necessary to inhibit the polymerization of the methacrylic acid during its final purification step. This can be done very effectively by using a combination of 100 parts per million of phenothiazine and 250 parts per million of p-benzoquinone based on the amount of methacrylic acid. This inhibitor system is added to the distillation zone at any time prior to or during the final purification of the methacrylic acid. It is to be understood, however, that other inhibitors can be used and that the particular inhibitor system described is a preferred system. Likewise, polymerization inhibitors may be present in the distillation zone in the first step of the formaldehyde concentration in order to prevent the polymerization of formaldehyde.

The process herein described can be more fully explained by referring to the flow chart in the drawing. The flow chart shows the process when carried out in a continuous fashion. The crude aqueous effluent is sent from the condensation reactor via 10, to the extractor 11. Recycled organic extraction solvent is sent to extractor 11 by way of 16. Upon achieving equlibrium two layers are obtained, an organic layer and an aqueous raffinate. The organic layer is removed and sent via 12 to the first distillation column 13. There, extraction solvent is stripped off along with the propionic acid/organic solvent azeotrope. The organic solvent/azeotrope distillate is taken overhead via 14 for separation into upper and lower phases in separator 15. The upper phase, containing organic solvent, 90-95% of the unreacted propionic acid taken overhead in the distillate and traces of water, formaldehyde and methacrylic acid, is recyced via 16 to the extractor to be used as extraction solvent. The lower phase, containing remaining unreacted propionic acid taken overhead in the distillate, the remaining unreacted formaldehyde taken overhead, water and traces of solvent and methacrylic acid, is sent, via 17 to be processed with the aqueous raffinate obtained in the extraction step. The bottoms left in column 13, containing methacrylic acid and any remaining unreacted propionic acid not taken overhead, are sent via 18 to a second distillation column 19, for final purification of methacrylic acid. Distillation in 19 yields, as overhead, any unreacted propionic acid remaining in the bottoms from column 13. This overhead is sent, via 20, to the condensation reactor for further reaction to methacrylic acid. The bottoms are highly pure methacrylic acid (about 95%) which is removed via 21 as a product stream.

The aqueous raffinate obtained during the extraction is sent via 22 to the first formaldehyde concentrator 23. There the aqueous raffinate is azeotropically distilled with an organic solvent entrainer to remove, as overhead, approximately 16% aqueous formaldehyde, water and entrainer. This overhead is sent via 25 to separator 26, where organic solvent entrainer separates and is fed back to column 23 by way of 27, while the dilute aqueous formaldehyde is sent via 28 to a second distillation column 29 for further concentration. The bottoms of the first formaldehyde concentration, containing about 50% aqueous formaldehyde and any unreacted propionic acid not extracted into the organic layer during the extraction, are recycled to the reaction condenser via 24 for further production of methacrylic acid. The dilute formaldehyde stream taken overhead in the first formaldehyde concentrator 23 and fed to the second concentrator 29, is distilled under pressure to obtain an overhead distillate of about 35% aqueous formaldehyde. This overhead is then sent via 30 and 22 to the first concentrator 23 for processing with further aqueous raffinate. The bottoms of this second concentration are aqueous waste which are disposed of via 31.

The invention is further illustrated by the following example, which is meant to be illustrative only and is not meant to delineate the scope of the invention nor limit the ambit of the claims.

EXAMPLE I

Parts are expressed as parts by weight, unless otherwise stated.

Process crude, having a composition of approximately 14% formaldehyde, 29% water, 35 propionic acid, 20% methacrylic acid and 1.5% by-products is first extracted with a 0.4 weight ratio of xylene using 5-6 theoretical stages. At equilibrium, the xylene used for extraction is recycled solvent containing about 29% propionic acid.

The organic layer from the extraction step has a composition of approximately 1% formaldehyde, 2% water, 28% propionic acid, 23% methacrylic acid and 46% xylene. This mixture is azeotropically fractionated in a 25-plate Oldershaw column at a 1:1 reflux ratio and a reduced pressure of 200 mm Hg. Feed is to the 15th plate from the bottom of the column. Temperatures are about 120° C. in the reboiler and about 88° C. in the vapor. The distillate is two phase, the upper, which is recycled to the extraction step, has an approximate composition of 2% methacrylic acid, 30 propionic acid, 67% xylene, 0.3% formaldehyde and 0.8% water. The lower phase, which is processed in the foramldehyde concentration step, has an approximate compsition of 0.4% methacrylic acid, 41% propionic acid, 3% xylene, 20% formaldehyde and 35% water.

The bottoms of this azeotropic solvent recovery step, containing about 73% methacrylic acid, 26% propionic acid and some high boilers, are fractionated to obtain esterification grade methacrylic acid containing about 0.1% propionic acid, as a bottoms stream. The distillation is performed in a 25-30 plate Oldershaw column operated at a 2:1 reflux ratio and a reduced pressure of 100 mm Hg, while temperatures are in the range of 112°-115° C. in the reboiler and 86°-88° C. in the vapor. An inhibitor system of 100 ppm of phenothiazine and 250 ppm p-benzoquinone, based on amount of methacrylic acid to be purified, is used in the boiler pot and in the distillation column to prevent polymerization of methacrylic acid. The overhead distillate, containing about 96% propionic acid and 4% methacrylic acid, is recycled to the condensation reactor.

The aqueous raffinate from the extraction has an approximate composition of 20% formaldehyde, 30% water, 40% propionic acid, 1% xylene and 0.3% methacrylic acid (based on extraction using recycled xylene). The raffinate is first concentrated to 50% aqueous formaldehyde by azeotropic distillation using toluene as the entrainer. The distillation is in a 25-plate Oldershaw column operated at 100-400 mm Hg; feed is to the 10th plate from the bottom of the column. The recovery of formaldehyde is 80% in the bottoms concentrate. The approximate compositions are: bottoms concenrate (50% aqueous formaldehyde) — 25% formaldehyde, 25% water, 50% propionic acid; overhead —10% formaldehyde, 87% water, 3% xylene.

In the second formaldehyde concentration, the dilute formladehyde taken overhead in the first concentration step is concentrated to about 35% aqueous formaldehyde and is recycled to the toluene azeotropic column of the first concentration step. The distillation is preformed at a pressure of about 2600 mm Hg gauge and a reflux ratio of 15:1. The bottoms, which contain very little organics, are discarded.

We claim:

1. A process for the recovery of methacrylic acid from an aqueous effluent produced by the vapor phase condensation of formaldehyde and propionic acid, said effluent further containing unreacted formaldehyde and propionic acid, where the recovery comprises:

a. contacting the aqueous effluent with an organic solvent having a high extractive efficiency for methacrylic acid, a low extractive efficiency for formaldehyde and water and capable of preferentially extracting and azeotroping with propionic acid, to obtain an organic layer and an aqueous raffinate;

b. distilling the organic layer obtained in step (a) to azeotropically remove about 50-100% of the unreacted propionic acid extracted by the organic solvent and to strip off the organic solvent, leaving as bottoms a mixture of methacrylic acid and remaining unreacted propionic acid;

c. distilling the bottoms of step (b) to obtain any remaining propionic acid overhead and pure methacrylic acid as bottoms;

d. azeotropically distilling the aqueous raffinate of step a) with an entrainer to obtain water and formaldehyde overhead and formaldehyde/propionic acid bottoms.

e. sending the overhead of step (d) to a separator to allow entrainer to separate from the water/formaldehyde taken overhead; and f. distilling the water/formaldehyde overhead obtained in step e. to concentrate the formaldehyde for recycle to step (d), while disposing of the aqueous bottoms as organic waste.

2. The process of claim 1, where the organic solvent is xylene.

3. The process of claim 1 where the organic solvent is n-octane.

4. The process of claim 1, where the entrainer is benzene.

5. The process of claim 1, where the entrainer is toluene.

6. The process of claim 1, where the distillation of step (b) yields an overhead having two phases, an upper organic phase which is recycled to step (a) and a lower aqueous phase which is proccessed with the raffinate of step (a).

7. The process of claim 1, where the distillation of step (b) is conducted at a pressure of about 180–200 mm Hg, and a bottoms temperature of about 115°–125° C.

8. The process of claim 1, where step (C) is a fractional distillation carried out at a pressure of about 100 mm Hg and a temperature of about 112°–115° C.

9. The process of claim 1, where the azeotropic distillation of step (d) is performed at a pressure of about 100–400 mm Hg and temperature in the range of 60°–90° C.

10. The process of claim 1, where the distillation of step (f) is carried out at a pressure of about 2600 mm Hg gauge.

11. The process of claim 1, where step (a) is performed using a 0.4 weight ratio of organic solvent to aqueous effluent.

12. The process of claim 1, where the distillation of step (d) is performed in the presence of polymerization inhibitor in the distillation zone.

13. A continuous process for recovery of methacrylic acid from an aqueous effluent produced by vapor phase condensation of formaldehyde and propionic acid, said effluent further containing unreacted formaldehyde and propionic acid, where the recovery comprises:

a. contacting the aqueous effluent with xylene at a 0.4 weight ratio of xylene to effluent, at equilibrium, an organic layer and an aqueous raffinate;

b. distilling, at about 200 mm Hg pressure and a bottoms temperature of about 120°0 C., the organic layer obtained in step (a) to remove overhead about 50–100% of unreacted propionic acid in xylene as a two phase azeotrope with an upper organic phase and a lower aqueous phase, and leaving as bottoms a mixture of methacrylic acid and remaining unreacted propionic acid;

c. recycling the upper organic phase of the azeotrope taken overhead in step (b) to step (a) and the lower aqueous phase of the azeotrope to the aqueous raffinate of step (a);

d. distilling, at a pressure of about 100 mm Hg, at a temperature of about 112–115° C. and in the presence of polymerization inhibitors, the bottoms of step (b) to obtain any remaining unreacted propionic acid overhead and pure methacrylic acid as bottoms;

e. recycling the overhead obtained in step (d) for condensation reaction to produce further methacrylic acid;

f. azeotropically distilling at about 100–400 mm Hg of pressure and temperature in the range of 60°–90° C., the aqueous raffinate of step (a) with a benzene entrainer to obtain an overhead of unreacted aqueous formaldehyde of about 16% concentration and bottoms consisting of unreacted formaldehyde in about 50% aqueous concentration and unreacted propionic acid, the bottoms being recycled for condensation reaction to produce further methacrylic acid; and g. sending the overhead of step (f) to a separator to allow the benzene entrainer to separate from the unreacted aqueous formaldehyde taken overhead; and h. distilling, at a pressure of 2600 mm Hg gauge, the 16% aqueous formaldehyde obtained in step (g) to concenrate the formaldehyde to about 35% aqueous concentration taking it overhead and recycling it to step (f), while disposing of the aqueous bottoms.

* * * * *